United States Patent
LaBarge et al.

(10) Patent No.: US 6,514,397 B2
(45) Date of Patent: Feb. 4, 2003

(54) GAS SENSOR

(75) Inventors: William J. LaBarge, Bay City, MI (US); Darrell H. Eldridge, Clarkston, MI (US); Paul Casey Kikuchi, Fenton, MI (US); Richard Eugene Fouts, Grand Blanc, MI (US); Richard Frederick Beckmeyer, Davisburg, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/747,369

(22) Filed: Dec. 21, 2000

(65) Prior Publication Data

US 2002/0108854 A1 Aug. 15, 2002

(51) Int. Cl.$^7$ .............................................. G01N 27/407
(52) U.S. Cl. ........................ 204/424; 204/421; 204/427
(58) Field of Search ................... 204/421–429

(56) References Cited

U.S. PATENT DOCUMENTS

| | | | |
|---|---|---|---|
| 4,177,112 A | * | 12/1979 | Suzuki et al. |
| 4,257,863 A | * | 3/1981 | Hoffman |
| 4,851,105 A | * | 7/1989 | Ishiguro et al. |
| 5,660,661 A | * | 8/1997 | Sugiyama et al. |
| 5,716,507 A | * | 2/1998 | Tanaka et al. |

OTHER PUBLICATIONS

Yamana, K; Weppner, W.; Kopp A; Yoshimura, T; "Microstructure and Electrical Resistance of Alumina–Doped Yttria–Stabilized Zirconia", Journal of Materials Science (UK), vol. 10, No. 20, pp. 1205–1207, Oct. 15, 1991; ISSN 0261–8028.

* cited by examiner

*Primary Examiner*—T. Tung
(74) *Attorney, Agent, or Firm*—Vincent A. Cichosz

(57) ABSTRACT

An exhaust gas sensor includes a first electrode, a second electrode, and an electrolyte disposed between the first electrode and the second electrode. The electrolyte includes a first portion disposed at least in partial physical contact and in ionic communication with a second portion. The first portion has a first portion grain size which is different than a second portion grain size. Further, a method for manufacturing a gas sensor includes forming a multiple portion electrolyte. The electrolyte is formed with a first portion having one grain size, and a second portion at least in partial physical contact and in ionic contact with the first portion, the second portion having a second portion grain size different from the first portion grain size. The electrolyte may be fired before or after application of an electrode in ionic contact with the first portion and a second electrode in ionic contact with said second portion.

15 Claims, 1 Drawing Sheet

GAS SENSOR

TECHNICAL FIELD

This disclosure relates generally to gas sensors, and, more particularly, to oxygen sensors for exhaust systems of mobile vehicles.

BACKGROUND

Gas sensors are used in the automotive industry to sense the composition of exhaust gases such as oxygen, hydrocarbons, and oxides of nitrogen, with oxygen sensors measuring the amounts of oxygen present in exhaust gases relative to a reference gas, such as air. A switch type oxygen sensor, generally, comprises an ionically conductive solid electrolyte material, a sensing electrode which is exposed to the exhaust gas, and a reference electrode which is exposed to the exhaust gas, and a reference electrode which is exposed to the reference gas. It operates in potentiometric mode, where oxygen partial pressure differences between the exhaust gas and reference gas on opposing faces of the electrochemical cell develop an electromotive force, which can be described by the Nernst equation:

$$E = \left(\frac{RT}{4F}\right) \ln\left(\frac{(Po_2)_{ref}}{(Po_2)}\right)$$

where:
E=electromotive force
R=universal gas constant
F=Faraday constant
T=absolute temperature of the gas
$(Po_2)$ref=oxygen partial pressure of the reference gas
$(Po_2)$=oxygen partial pressure of the exhaust gas The large oxygen partial pressure difference between rich and lean exhaust gas conditions creates a step-like difference in cell output at the stoichiometric point; the switch-like behavior of the sensor enables engine combustion control based on stoichiometry. Stoichiometric exhaust gas, which contains unburned hydrocarbons, carbon monoxide, and oxides of nitrogen, can be converted very efficiently to water, carbon dioxide, and nitrogen by automotive three-way catalysts in automotive catalytic converters. In addition to their value for emissions control, the sensors also provide improved fuel economy and drivability.

The solid electrolyte commonly used in exhaust sensors is yttria-stabilized zirconia, which is an excellent oxygen ion conductor. The electrodes are typically platinum-based and porous in structure to enable oxygen ion exchange at electrode/electrolyte/gas interfaces. These platinum electrodes may be co-fired or applied to a fired (densified) electrolyte element in a secondary process, such as sputtering, plating, dip coating, etc. These electrodes can be made in the form of a film, paste, or ink and applied to the solid ceramic electrolyte in several ways. The electrode is added either before the ceramic is fired (green), before the ceramic is fully fired (bisque) or after the ceramic is fully fired. Once the electrode is added and fired, a strong bond should result between the electrode and the ceramic body. In the case of an oxygen sensor, poor bonding between the platinum and the yttrium stabilized zirconia body can result in poor adhesion leading to poor sensor performance and unacceptable durability.

The poor adhesion is due to the different coefficients of thermal expansion between the electrodes, the electrolyte, and the porous protective coating. For example, the platinum electrode has a different thermal expansion than the yttria-zirconia electrolyte. The varying degrees of thermal expansion results in a "pulling" phenomenon between the electrode and the electrolyte, increasing the debonding at the platinum and zirconia interface.

Furthermore, an electrical resistance between the electrode and the electrolyte exists in each of the electrochemical cells. Minimizing this resistance generally will result in an increase in the resultant electromotive force due to oxygen concentration variation between the exhaust gas and a reference gas. Reducing the applied voltage also has the effect of increasing the useful life of the sensors.

Additionally, impurities (also referred to as "poisons") within the electrolyte flux to the outer surface of the electrolyte upon firing. This is particularly of concern where the electrode is added either before the ceramic is fully fired or after the ceramic is fully fired. The poison interferes with both the adhesion and electrical resistance of the sensor.

While existing sensors are suitable for their intended purposes, there still remains a need for improvements, particularly regarding the electrical and mechanical interface between the electrode and the electrolyte.

SUMMARY

The drawbacks and disadvantages of the prior art are overcome by the exhaust gas sensor including a first electrode, a second electrode, and an electrolyte disposed between said first electrode and said second electrode, wherein the electrolyte includes a first portion disposed at least in partial physical contact and in ionic communication with a second portion, the first portion having a first portion grain size which is different than a second portion grain size.

A method for manufacturing a gas sensor includes forming a multiple portion electrolyte. The electrolyte is formed with a first portion having one grain size, and a second portion at least in partial physical contact and in ionic contact with the first portion, the second portion having a second portion grain size different from the first portion grain size. The electrolyte may be fired before or after application of an electrode in ionic contact with the first portion and a second electrode in ionic contact with said second portion

BRIEF DESCRIPTION OF THE DRAWINGS

Referring now to the figure, which is meant to be exemplary not limiting.

DETAILED DESCRIPTION

Figure 1:
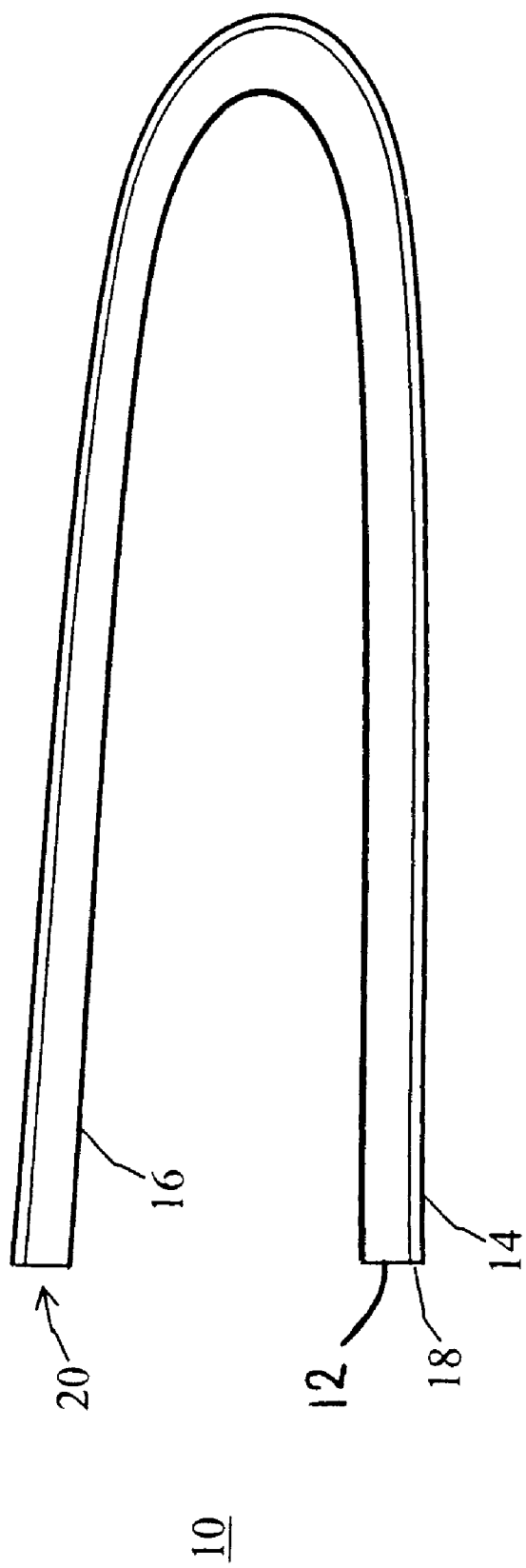
FIG. 1 is an exploded view of an exemplary embodiment of an exhaust gas sensor.

A gas sensor element is described herein, wherein the sensor element includes an electrochemical cell that produces a quantity of oxygen ions upon exposure to a gas stream containing oxygen, wherein the ions generate a current which is generally proportional to the oxygen concentrations in the gas stream. It will be understood that although the apparatus and method are described in relation to an oxygen sensor, the sensor is contemplated for use as a nitrogen oxide sensor, a hydrocarbon sensor, a sulfur oxides sensor, a carbon monoxide sensor or the like, for detecting components in gases such as smokestacks, chimneys, furnaces, smelting equipment, exhaust systems, and the like.

FIG. 1 shows an exemplary embodiment of a sensor element 10 comprising a solid electrolyte 20 in ionic contact with an electrode 14 (e.g., an exhaust gas electrode) and an electrode 16 (e.g., a reference electrode). The electrolyte has a first electrolyte portion 12 and a second electrolyte portion 18 in communication with the electrodes 16, 14, respectively. The electrodes 14, 16, and electrolyte 20 form an electrochemical cell.

The exhaust gas, possibly containing oxygen and other components, such as nitrogen oxides, diffuses through electrode 14. The reference gas, possibly outside air or a specialized reference feed, diffuses through electrode 16. A voltage is conducted across the electrolyte 20 that varies according to the difference in oxygen content between the exhaust gas and the reference gas.

Electrolyte 20 can be any material that is capable of permitting the electrochemical transfer of oxygen ions while inhibiting the physical passage of exhaust gases, that preferably possesses an ionic/total conductivity ratio of approximately unity, and that is compatible with the environment in which the sensor will be utilized (e.g., temperatures up to about 1,000° C.). Possible solid electrolyte materials include conventional materials, e.g., metal oxides such as zirconia, alumina, and the like which may optimally be stabilized with yttria, calcia, magnesium, calcium, yttrium, aluminum, lanthanum, cesium, gadolinium, among other materials and oxides thereof, and combinations comprising at least one of the foregoing electrolyte materials. For example, the solid electrolyte material can be yttria-stabilized zirconia, with a concentration of about 2 to about 14 weight percent (wt. %) yttria preferred, and a concentration of about 3 to about 12 wt. % yttria most preferred, based upon the total weight of the electrolyte 20.

In order to attain the desired structural integrity, first portion 12 preferably comprises fine metal oxide particles or a mixture of metal oxide particles having fine and large grain sizes. Typically, the thickness of the first portion 12 is up to about 1,600 microns, with a thickness of about 400 microns to about 1,200 microns preferred, and a thickness of about 800 to about 1,000 microns especially preferred. The metal oxide particles in the first portion 12 generally have grain sizes up to about 12 microns, with grain sizes of about 0.1 microns to about 8 microns preferred, and grain sizes of about 0.2 to about 2 microns especially preferred. Further, the electrolyte material within the first portion 12 is yttria-stabilized zirconia, with a concentration of about 2 to about 10 wt. % yttria preferred, and a concentration of about 3 to about 6 wt. % yttria most preferred, based upon the total weight of the electrolyte material of first poriton 12.

In contrast to first portion 12, the second portion 18, preferably is thinner than first portion 12 and has a coarser particle size. Typically, the thickness of the second portion 18 is up to about 100 microns, with a thickness of about 10 microns to about 70 microns preferred, and a thickness of about 20 to about 50 microns especially preferred. The grain size of second portion 18 is at least about 4 microns, with grain sizes of about 5 microns to about 12 microns preferred, and grain sizes of about 7 to about 10 microns especially preferred. Further, the electrolyte material within the second portion 18 is yttria-stabilized zirconia, with a concentration of about 6 wt. % to about 14 wt. % yttria preferred, and a concentration of about 8 to about 12 wt. % yttria most preferred, based upon the total weight of the electrolyte material of second portion 18.

Optionally, another electrolyte portion (not shown) similar to the second portion 18 may be formed between the electrolyte 20 and electrode 16. The additional portion may comprise the same materials and be formed with similar dimensions as the second portion 18, or may comprise different materials and/or be formed with different dimensions as the second portion 18.

In order to reduce resistance between the exhaust electrode 14 and the electrolyte 20, the electrolyte 20 has two portions, the first portion 12 and the second portion 18. Each portion 12 and 18 comprise a different range of grain sizes.

In one embodiment, the different grain sizes result from different yttria concentrations in the yttria-stabilized zirconia electrolyte material. Generally, the yttria concentration is a determining factor for transformation of the zirconia to monoclinic, cubic, tetragonal phases, or a combination comprising at least one of the foregoing phases. Lower concentration of zirconia generally results in primarily a monoclinic phase. A mixture of monoclinic, cubic, and tetragonal phases are generally preferred in the portion 12. Larger yttrium oxide particles interacting with smaller zirconium particles typically results in a range of yttria-zirconia concentrations. The various range yttria-zirconia concentrations typically causes a range of volume expansions from various degrees of expansion to no expansion at all. As the temperature changes, one phase may stop expanding or contracting, and another phase will start expanding or contracting.

In the second portion 18, a higher yttria concentration range (relative to the yttria concentration range in the first portion 12) is preferably used to attain larger grain sizes. The yttria is preferably uniformly distributed throughout the yttria-zirconia electrolyte material of the second portion 18. Larger grain sizes generally correspond with increased ionic conductivity. Preferably, the grains in the second portion are primarily in a cubic phase.

The electrolyte 20 can be formed using conventional techniques such as molding, grinding, die pressing, roll compaction, sintering, extrusion, sputtering, chemical vapor deposition, screen printing, stenciling, combinations comprising at least one of the foregoing techniques, and the like. Preferably, to maintain the differently sized grains in the first portion 12 and the second portion 18, the higher yttria concentration electrolyte material of the second portion 18 is present during a firing step. In one embodiment, the second portion 18 is formed on the first portion 12 by coating the first portion with a yttria-zirconia powder (which will form the second portion 18) dispersed in an organic such as ethanol. The organic typically will be adsorbed in the electrolyte of the first portion 12, resulting in the second portion 18 adhering to the first portion 12. Permanent adhesion of the first portion and the second portion is attained upon firing.

Disposed on opposite sides of electrolyte 20 are electrodes 14, 16. Electrodes 14, 16 can comprise any catalyst capable of ionizing oxygen, including, but not limited to, noble metal catalysts (such as gold, platinum, palladium, rhodium, ruthenium, osmium, iridium, and the like), metal oxides, and mixtures and alloys comprising at least one of the foregoing catalyst materials.

Typically, the size of electrodes 14, 16 is adequate to provide current output sufficient to enable reasonable signal resolution over a wide range of air/fuel ratios. Generally, a thickness of about 1.0 to about 25 microns can be employed, with a thickness of about 5 to about 20 microns preferred, and about 10 to about 18 microns more preferred. The geometry of the electrodes 14, 16 is generally conical.

Electrodes 14, 16 can be formed using conventional techniques such as sputtering, chemical vapor deposition, screen printing, stenciling, dipping, combinations comprising at least one of the foregoing techniques, and the like, with sputtering preferred.

Sensor element 10 may be manufactured using conventional techniques as detailed above. For example, the electrolyte 20 may be formed and fired, wherein electrodes 14, 16 are formed subsequently. Alternatively, the electrolyte 20 and one or both of the electrodes 14, 16 may be formed, and the electrolyte 20 and electrode 14 and/or 16 co-fired. The firing temperature is generally about 900° C. to about 2000° C., preferably about 900° C. to about 1500° C., and more preferably about 1,000° C. to about 1500° C.

When the structure is fired, various poisons flux to the outer surface of the fired structure. In circumstances where the electrolyte 20 is fired and electrode 14 and/or 16 is subsequently deposited, the poisons are present at the interface. However, with the inclusion of the electrolyte portion described herein having coarser grain sizes as compared to the remainder of the electrolyte, any detriment attributable to the poisons is minimized. The poisons typically reside between individual metal oxide grains. Since the grains are courser at one or both of the surfaces of the electrolyte, poisons generally settle to regions between grains. The grains, therefore, have areas available lacking poison for electrode adherence.

For placement in a gas stream, sensor element 10 can be disposed within a protective casing having holes, slits or apertures, generally to limit the overall exhaust gas flow contacting sensor element 10. This arrangement extends the useful life of sensor element 10 by minimizing the ion transport through the electrodes and electrolyte. Furthermore, any shape can be used for the sensor element 10, including conical, tubular, rectangular, and flat, and the like, and the various components, therefore, will have complementary shapes, such as in plan views, circular, oval, quadrilateral, rectangular, or polygonal, among others.

In addition to the above-described components, the sensor element 10 can further comprise a heater (not shown) disposed within the sensor, adjacent to electrode 16. The heater can be any conventional heater typically employed in sensor applications, such as platinum and the like. The sensors are capable of operation with a heater having a power requirement of generally less than about 12 watts, preferably less than about 10 watts, and more preferably less than about 7 watts.

EXAMPLE

In one example of a gas sensor, a first electrolyte portion may be molded and ground into the desired shape. The first portion comprises yttria-stabilized zirconia having about 5 wt. % yttria. A second electrolyte portion can be formed on the first portion by deposition, and comprises yttrium-stabilized zirconia having about 10 wt. % yttria. An outer electrode was sputtered, and an inner electrode was inked on the electrolyte. The sensor was fired to about 1000 C.

Electrical performance testing comprised impedance measurements at about 800° C. Consequently, the sensor of the present invention reduces the impedance from above about 1,200 ohms for conventional sensors to below about 300 ohms for the sensor including the electrolyte layer, with below about 200 ohms preferred, and below about 80 ohms especially preferred.

The gas sensor described herein improves the detection and measurement of oxygen concentrations and partial pressures, in several advantageous ways. The gas sensor provides an enhanced adhesion between the electrode layer and the electrolyte material.

Also, the exhaust gas sensor described herein having the electrolyte layer also provides less resistance between the electrode and the electrolyte. The lower resistance allows for measurements with a higher degree of sensitivity. In a sensor described in Example 1, the light off temperature was reduced by at least 30° C. and the light off time was reduced by at least 4 seconds, as compared to conventional sensors.

Generally, the enhanced adhesion and lower resistance also results in a longer lasting sensor. Durability increased by at least 30% measured at the point where electrode resistance increased at testing at 800° C. with a 12:1 air to fuel ratio.

While preferred embodiments have been shown and described, various modifications and substitutions may be made thereto without departing from the spirit and scope of the invention. Accordingly, it is to be understood that the apparatus and method have been described by way of illustration only, and such illustrations and embodiments as have been disclosed herein are not to be construed as limiting to the claims.

What is claimed is:

1. A gas sensor, comprising;
a first electrode and a second electrode;
an electrolyte disposed between said first electrode and said second electrode, wherein said electrolyte comprises a first portion disposed at least in partial physical contact and in ionic communication with a second portion, said first portion having a first portion grain size and said second portion having a second portion grain size, wherein said first portion is thicker than said second portion, and wherein said first portion grain size is smaller than said second portion grain size.

2. The sensor recited in claim 1, wherein said first portion grain size is less than 12 microns.

3. The sensor recited in claim 1, wherein said second portion grain size is at least about 4 microns.

4. The sensor recited in claim 1, wherein said electrolyte further comprises a third portion disposed at least in partial physical contact and in ionic communication with said first portion, wherein said first portion grain size is different from a third portion grain size.

5. The sensor recited in claim 4, wherein said first portion grain size is less than 12 microns.

6. The sensor recited in claim 4, wherein said second portion grain size is at least about 4 microns.

7. The sensor recited in claim 4, wherein said third portion grain size is at least about 4 microns.

8. The sensor recited in claim 1, wherein said electrolyte has a shape that is conical, tubular, rectangular, or flat.

9. The sensor recited in claim 1, wherein said electrolyte has a shape that is conical.

10. The sensor recited in claim 9, wherein said first electrode is disposed on an inside facing surface of said electrolyte and said second electrode is disposed on an outside facing surface of said electrolyte.

11. The sensor recited in claim 10, wherein said second portion is in ionic communication with said second electrode.

12. The sensor recited in claim 11, wherein said electrolyte further comprises a third portion disposed at least in partial physical contact and in ionic communication with said first portion, said first portion said third portion having a third portion grain size, wherein said first portion grain size is different from said third portion grain size.

13. The sensor recited in claim 12, wherein said third portion is in ionic communication with said first electrode.

14. The sensor recited in claim 10, wherein said first portion grain size is less than 12 microns.

15. The sensor recited in claim 14, wherein said second portion grain size is at least about 4 microns.

* * * * *